United States Patent

Bentley

[11] 4,416,883
[45] Nov. 22, 1983

[54] PENICILLIN DERIVATIVES

[75] Inventor: Peter H. Bentley, Horsham, England

[73] Assignee: Beecham Group Limited, England

[21] Appl. No.: 277,031

[22] Filed: Jun. 24, 1981

[30] Foreign Application Priority Data

Jun. 26, 1980 [GB] United Kingdom ............... 8020954

[51] Int. Cl.³ ................. A61K 31/495; C07D 499/70
[52] U.S. Cl. ................................ 424/250; 260/239.1
[58] Field of Search ................... 260/239.1; 424/250

[56] References Cited

U.S. PATENT DOCUMENTS

| | | | |
|---|---|---|---|
| 3,487,074 | 12/1969 | Sheehan | 260/239.1 |
| 4,087,424 | 5/1978 | Saikawa et al. | 260/239.1 |
| 4,166,817 | 9/1979 | Ferres et al. | 260/239.1 |
| 4,215,118 | 7/1980 | Preiss et al. | 260/239.1 |
| 4,235,774 | 11/1980 | Preiss et al. | 260/239.1 |

Primary Examiner—Natalie Trousof
Assistant Examiner—Vera C. Clarke
Attorney, Agent, or Firm—Jacobs & Jacobs

[57] ABSTRACT

A compound of formula (I) or a pharmaceutically acceptable salt or in vivo hydrolysable ester thereof:

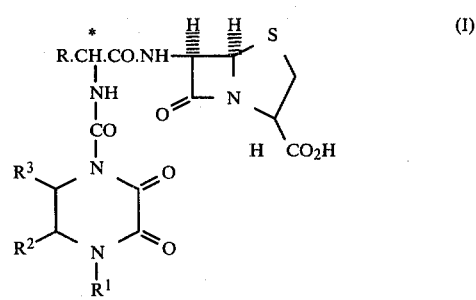

wherein R is phenyl, 4-hydroxy phenyl, or a 5- or 6-membered heterocyclic ring containing up to three heteroatoms selected from oxygen, sulphur or nitrogen, optionally substituted with hydroxy, amino, halogen or $C_{1-6}$ alkoxy;

$R^1$ represents hydrogen or $C_{1-6}$ alkyl;

$R^2$ and $R^3$ are the same or different and represent hydrogen, $C_{1-6}$ alkyl, halogen, amino, hydroxy, or $C_{1-6}$ alkoxy.

Their preparation and use is described.

9 Claims, No Drawings

PENICILLIN DERIVATIVES

This invention relates to a class of penicillin derivatives which have antibacterial activity and are of value in the treatment of infections in animals, including man and poultry, caused by a wide range of organisms, particularly Gram-negative organisms. In particular the invention relates to a class of bis nor penicillin derivatives. The invention also relates to a process for the preparation of such compounds, and to pharmaceutical compositions comprising them.

British Patent Specification No. 1,546,622 discloses inter alia a class of compounds of the formula (A):

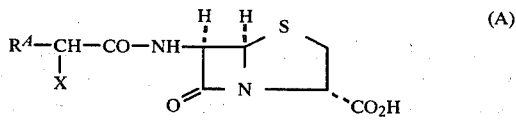

and pharmaceutically acceptable salts and in-vivo hydrolysable esters thereof wherein $R^A$ is a phenyl, 4-hydroxyphenyl, 2-thienyl or 3-thienyl group and X is an amino, hydroxyl, carboxyl or $C_{1-7}$ esterified carboxyl group.

We have now found a class of penicillins lacking the gem-dimethyl groups in the nucleus (referred to as "bis-nor penicillins") which have a high level of anti-bacterial activity against gram-negative organisms.

According to the present invention there is provided a compound of formula (I) or a pharmaceutically acceptable salt or in vivo hydrolysable ester thereof:

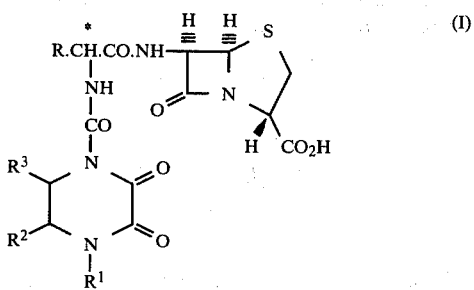

wherein R is phenyl, 4-hydroxy phenyl, or a 5- or 6-membered heterocyclic ring containing up three heteroatoms selected from oxygen, sulphur or nitrogen, optionally substituted with hydroxy, amino, halogen or $C_{1-6}$ alkoxy;

$R^1$ represents hydrogen or $C_{1-6}$ alkyl;

$R^2$ and $R^3$ are the same or different and represent hydrogen, $C_{1-6}$ alkyl, halogen, amino, hydroxy, or $C_{1-6}$ alkoxy.

The compounds of the present invention include the pharmaceutically acceptable esters of compound (I) which hydrolyse readily in the human body to produce the parent acid, for example acyloxyalkyl groups such as acetoxymethyl, pivaloyloxymethyl, α-acetoxyethyl, α-acetoxyethyl and α-pivaloyloxyethyl groups; alkoxycarbonyloxyalkyl groups, such as ethoxycarbonyloxymethyl and α-ethoxycarbonyloxyethyl; dialkylaminoalkyl groups such as dimethylaminomethyl, dimethylaminoethyl, diethylaminomethyl or diethylaminoethyl; and lactone groups such as phthalidyl or dimethoxyphthalidyl.

Suitable salts of the compound of formula (I) include metal salts e.g. aluminium, alkali metal salts such as sodium or potassium alkaline earth metal salts such as calcium or magnesium and ammonium or substituted ammonium salts, for example those with lower alkylamines such as triethylamine, hydroxy-lower alkylamines such as 2-hydroxyethylamine, bis-(2-hydroxyethyl)-amine or tri-(2-hydroxyethyl)-amine, cycloalkylamines such as bicyclohexylamine, or with procaine, dibenzylamine, N,N-dibenzylethylenediamine, 1-ephenamine, N-ethylpiperidine, N-benzyl-β-phenethylamine, dehydroabietylamine, N,N'-bisdehydroabiethylamine ethylenediamine, or bases of the pyridine type such as pyridine, collidine or quinoline, or other amines which have been used to form salts with known penicillins.

The carbon atoms marked * in formula (I) is asymmetric so that the compounds may exist as two optically active diastereoisomers. In general that prepared from the D-side chain exhibits the highest antibacterial activity.

In formula (I), the group R is preferably phenyl, 4-hydroxyphenyl, 2-thienyl, 3-thienyl or 2-amino-4-thiazolyl.

Suitable $C_{1-6}$ alkyl groups for the groups $R^1$, $R^2$ and $R^3$ include methyl, ethyl, n- and iso-propyl, n, sec-, iso- and tert-butyl. Preferably $R^1$ is ethyl.

Preferably $R^2$ and $R^3$ are hydrogen.

Specific compounds within this invention include the following:

6,β[D,2(4-ethyl-2,3-dioxopiperazine-1-carbonylamino)]phenylacetamido bis nor penicillanic acid;

6,β[2,4(ethyl-2,3-dioxopiperazine-1-carbonylamino)]-thien-2-ylacetamido bis nor penicillanic acid; and 6,β[D,2(4-ethyl-2,3-dioxopiperazine-1-carbonylamino)2(4-hydroxyphenyl)]acetamido bis nor penicillanic acid.

The compounds of formula (I) may be prepared by reacting a compound of formula (II):

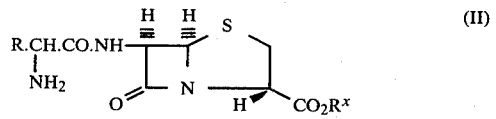

wherein the amino group is optionally substituted with a group which permits acylation to take place, R is as defined with respect to formula (I) and any reactive substituents may be protected, and $R^x$ is hydrogen or a carboxyl-blocking group, with an N-acylating derivative of an acid of formula (III).

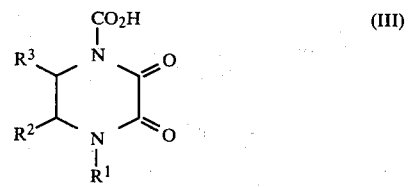

wherein $R^1$, $R^2$ and $R^3$ are as defined with respect to formula (I) above and any reactive groups may be protected; and thereafter, if necessary, carrying out one or more of the following steps:

(i) removing any carboxyl-blocking group $R^x$ (ii) removing any protecting groups on the side chain group;

(iii) converting the product into a salt or in vivo hydrolysable ester thereof.

Suitable groups which permit acylation to take place and which are optionally present on the amino group of the starting material of the formula (II) include N-silyl, N-stannyl and N-phosphorus groups, for example trialkylsilyl groups such as trimethylsilyl, trialkyltin groups such as tri-n-butyltin, groups of formula —P.$R^a R^b$ wherein $R^a$ is an alkyl, haloalkyl, aryl, aralkyl, alkoxy, haloalkoxy, aryloxy, aralkyloxy or dialkylamino group, $R^b$ is the same as $R^a$ or is halogen or $R^a$ and $R^b$ together form a ring; suitable such phosphorus groups being

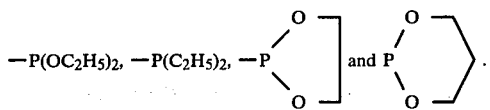

Suitable carboxyl-blocking derivatives for the group —$CO_2R^x$ in formula (II) include salts and ester derivatives of the carboxylic acid. The derivative is preferably one which may readily be cleaved at a later stage of the reaction. Suitable salts include metal salts, such as those with sodium, potassium and lithium, and tertiary amine salts, such as those with trilower-alkylamines, N-ethylpiperidine, 2,6-lutidine, pyridine, N-methylpyrrolidine, dimethylpiperazine. A preferred salt is with triethylamine.

Suitable ester-forming carboxyl-blocking groups are those which may be removed under conventional conditions. Such groups for $R^x$ include benzyl, p-methoxybenzyl, 2,4,6-trimethylbenzyl, 3,5-di-t-butyl-4-hydroxybenzyl, benzoylmethyl, p-nitrobenzyl, 4-pyridylmethyl, 2,2,2-trichloroethyl, 2,2,2-tribromoethyl, t-butyl, t-amyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, p-toluenesulphonylethyl, methoxymethyl, a silyl, stannyl or phosphorus-containing group, such as described above, an oxime radical of formula —N=CHR° where R° is aryl or heterocyclic, or an in vivo hydrolysable ester radical such as defined above.

The carboxyl group may be regenerated from any of the above esters by usual methods appropriate to the particular $R^x$ group, for example, acid—and base—catalysed hydrolysis, or by enzymically—catalysed hydrolysis, or by hydrogenation.

A reactive N-acylating derivative of the acid (III) is employed in the above process. The choice of reactive derivative will of course be influenced by the chemical nature of the substituents of the acid.

Suitable N-acylating derivatives include an acid halide, preferably the acid chloride or bromide. Acylation with an acid halide may be affected in the presence of an acid binding agent for example tertiary amine (such as triethylamine or dimethylaniline), an inorganic base (such as calcium carbonate or sodium bicarbonate) or an oxirane, which binds hydrogen halide liberated in the acylation reaction. The oxirane is preferably a ($C_{1-6}$)-1,2,alkylene oxide—such as ethylene oxide or propylene oxide. The acylation reaction using an acid halide may be carried out at a temperature in the range −50° C. to +50° C., preferably −20° to +20° C., in aqueous or non-aqueous media such as aqueous acetone, aqueous tetrahydroform, ethyl, acetate, dimethylacetamide, dimethylformamide, acetonitrile, dichloromethane, 1,2-dichloroethane, or mixtures thereof. Alternatively, the reaction may be carried out in an unstable emulsion of water-immiscible solvent, especially an aliphatic ester or ketone, such as methyl isobutyl ketone or butyl acetate.

The acid halide may be prepared by reacting a compound of formula IV:

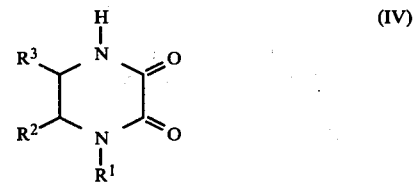

wherein $R^1$, $R^2$ and $R^3$ are as defined with respect to formula (I) with a silylating agent and thereafter treating the N-silyl derivative with phosgene or carbonyl dibromide.

Suitable silylating agents include halosilanes or silazanes of the formulae.

$L_3$ Si U; $L_2$ Si $U_2$; $L_3$ Si $NL_2$;

$L_3$ Si NH Si $L_3$; $L_3$ Si.NH.COL; $L_3$ Si.NH.CO.NH.Si $L_3$;

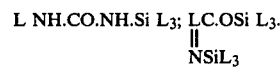

wherein U is a halogen and the various groups L which may be the same or different, each represents hydrogen or alkyl, alkoxy, aryl, or aralkyl. Preferred silylating agents are silyl chlorides, particularly trimethylchlorosilane, and dimethyldichlorosilane.

The intermediate compound of formula (II) may be prepared by reacting a compound of formula (V):

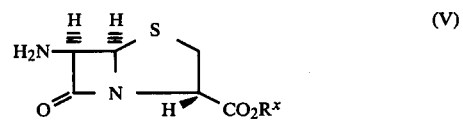

wherein the amino group is optionally substituted with a group which permits acylation to take place and $R^x$ is as defined with respect to formula (II) above, with an N-acylating derivative of an acid of formula (VI):

wherein R is as defined with respect to formula (I) and any reactive groups therein may be protected and $R^y$ is an amino-protecting group; and thereafter removing protection group $R^y$.

Suitable N-acylating derivatives, carboxyl protecting groups and reaction conditions include those described hereinbefore.

Suitable amino-protecting groups $R^y$ are those well-known in the art which may be removed under conventional conditions without disruption of the remainder of the molecule.

The starting material of formula (V) is disclosed in British Pat. No. 1,546,622.

The compounds of formula (I) may also be prepared by reacting a compound of formula (V) as described hereinbefore with an N-acylating derivative of an acid of formula (VII):

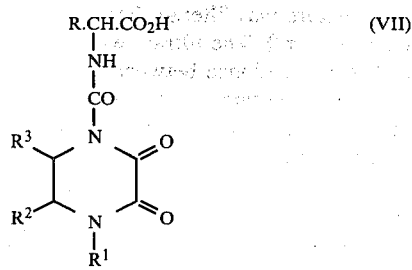

where R, $R^1$, $R^2$ and $R^3$ are as defined with respect to formula (I) and any reactive groups therein may be protected; and thereafter, if necessary, carrying out one or more of the following steps:
(i) removing any carboxyl-blocking group $R^x$
(ii) removing any protecting groups on the side chain group;
(iii) converting the product into a salt or in vivo hydrolysable ester thereof.

The antibiotic compounds according to the invention may be formulated for administration in any convenient way for use in human or veterinary medicine, by analogy with other antibiotics, and the invention therefore includes within its scope a pharmaceutical composition comprising a compound of formula (I) above together with a pharmaceutical carrier or excipient.

The compositions may be formulated for administration by any route, such as oral topical or parenteral. The compositions may be in the form of tablets, capsules, powders, granules, lozenges, creams or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine, tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, methyl cellulose, glucose syrup, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and if desired conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% by weight, preferably from 10-60% by weight, of the active material, depending on the method of administration. Where the compositions comprise dosage units, each unit will preferably contain from 50-500 mg of the active ingredient. The dosage as employed for adult human treatment will preferably range from 100 to 3000 mg per day, for instance 1500 mg per day depending on the route and frequency of administration.

The compound of formula (I) may be the sole therapeutic agent in the compositions of the invention or a combination with other antibiotics and/or a β-lactamase inhibitor may be employed. Advantageously the compositions also comprise a compound of formula (VIII) or a pharmaceutically acceptable salt or ester thereof:

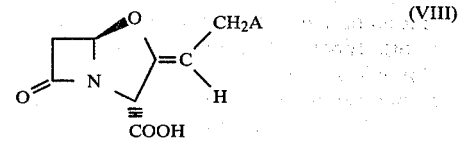

wherein A is hydroxyl, substituted hydroxyl, thiol, substituted thiol, amino, mono- or di-hydrocarbyl-substituted amino, or mono- or di-acylamino.

The following Examples illustrate the preparation of some of the compounds of this invention.

EXAMPLE 1

6,β[D,2(4-Ethyl-2,3-dioxopiperazine-1-carbonylamino)]-1-phenylacetamidobisnorpenicillanic acid (a) Benzyl 6,β-aminobisnorpenicillanate, p-toluene sulphonic acid salt A stirred solution of benzyl 6β-phenylacetamidobisnorpenicillanate (3.56 g, 8.9 mmol) in dry dichloromethane (15 ml) was cooled to −25° C. under nitrogen and treated with first, N-methylmorpholine (1.82 g, 1.97 ml, 17.98 mmol) and then, dropwise, with a solution of phosphorous pentachloride (2.25 g, 10.79 mmol) in dry dichloromethane (25 ml). The solution was stirred for 45 minutes during which time the temperature was allowed to reach 0° C. The mixture was then re-cooled to −25° C. and treated, dropwise, with dry methanol (40 ml, 0.9 mol). Stirring was continued for 2½ hours at 0° C. when the contents of the reaction vessel were poured into iced water (140 ml). The pH of the mixture was adjusted to 2 with 5 N ammonium hydroxide solution (0.5 ml) and vigorous stirring continued for 20 minutes, at 0° C. The pH was then raised to 6 with 5 N ammonium hydroxide solution and the organic layer separated. The aqueous phase was re-extracted with dichloromethane (50 ml) and the combined organic fractions were washed with saturated sodium bicarbonate solution (15 ml), brine (2×20 ml), dried over anhydrous magnesium sulphate and evaporated to give an orange gum. This crude product was dissolved in ethyl acetate (25 ml), treated with a solution of p-toluene sulphonic acid monohydrate (1.7 g, 8.9 mmol) in acetone (3 ml) and stored at −5° C. for 1 hour. The precipitated solid was collected by filtration, washed with ethyl acetate (5 ml), ether (10 ml) and dried to give benzyl 6,β-aminobisnorpenicillanate, p-toluenesulphonic acid salt, as a colourless solid (1.93 g, 48%), m.p. 170°–172° dec. (lit., 169°–170°; Vanderhaeghe et al, J. Med. Chem., 1974, 17, 4, 389; 163°–165°; Osborne, J.C.S. Perkin I, 1980, 150), $\nu_{max}$ (Nujol) 1790, 1750 cm$^{-1}$ [Nujol is a registered trade mark], δ [acetone-d$^6$+DMSO-d$^6$] 7.75 (2H, d, J 8 Hz), 7.45 (5H, s), 7.15 (2H, d, J 8 Hz), 5.50–5.10 (5H, m), 3.55 (2H, m) and 2.35 (3H, s) ppm.

(b) Benzyl 6,β[D,2(4-ethyl-2,3-dioxopiperazine-1-carbonylamino)]-phenylacetamidobisnorpenicillanate D,2(4-Ethyl-2,3-dioxopiperazine-1-carbonylamino)-phenylacetic acid (1.36 g, 4.2 mmol) in dry dichloromethane (15 ml) and N,N-dimethylformamide (2 drops) was cooled to 0° and treated dropwise, with oxalyl chloride (0.59 g, 0.41 ml, 4.6 mmol). The solution was stirred for 90 minutes during which time the temperature was allowed to rise to 21° C. The reaction mixture was then twice evaporated to c.a. 5 ml diluting with fresh, dry dichloromethane (10 ml) after each evaporation.

This acid chloride solution was added to a stirred solution of benzyl 6β-aminobisnorpenicillanate (1.1 g, 4 mmol), (liberated from the corresponding p-toluene sulphonic acid salt [1.9 g, 4.2 mmol] by the action of sodium bicarbonate solution), in dichloromethane (15 ml) at 0° C. under nitrogen in the presence of dry pyridine (0.4 g, 0.41 ml, 0.5 mmol). The mixture was stirred for 30 minutes at 0° and then for 1 hour at 21° C. when ethyl acetate (100 ml) and dilute hydrochloric acid (20 ml) were added. The separated organic phase was washed with saturated sodium bicarbonate solution (20 ml) followed by brine (20 ml) and was then dried over magnesium sulphate and evaporated to give a yellow gum. This crude product was dissolved in warm ethanol (5 ml), stored for 1 hour at −5° and the precipitated solid filtered, washed with ether and dried (1.2 g, 52%). Chromatographic separation of the mother liquor afforded a further quantity of product (0.2 g, 9%), m.p. 195°–196°, $\nu_{max}$ (Nujol) 3330, 3290, 1770, 1735, 1670 cm$^{-1}$, δ (CDCl$_3$) 10.11 (1H, d, J 7 Hz), 7.62–7.22 (11H, m), 5.64 (1H, dd, J 9 Hz and J 4 Hz), 5.48 (1H, d, J 7 Hz), 5.30–5.09 (3H, m), 4.95–4.81 (1H, m), 4.32–3.21 (8H, m) and 1.22 (3H, t, J 7 Hz) ppm.

(c) 6β-[D,2-(4-Ethyl-2,3-dioxopiperazine-1-carbonylamino)]-phenylacetamidobisnorpenicillanic acid, sodium salt Benzyl 6,β-[D,2-(4-ethyl-2,3-dioxopiperazine-1-carbonylamino)]-phenylacetamidobisnorpenicillanate (0.75 g, 1.3 mmol) in a mixture of dichloromethane (15 ml), ethanol (4 ml) and water (3 ml) was shaken under an atmosphere of hydrogen in the presence of 10% palladium on charcoal (0.75 g) for 15 minutes. A further quantity of catalyst (0.25 g) was then added and hydrogenolysis continued for a further 1 hour when the reaction mixture was filtered through celite, washing with ethanol (5 ml). The filtrate was evaporated to dryness and then partitioned between dichloromethane (15 ml) and dilute sodium bicarbonate solution (25 ml). The aqueous phase was separated, acidified to pH 1.5 with 5 N hydrochloric acid and extracted with ethyl acetate (3×50 ml). The combined organic extracts were washed with brine (25 ml), dried (MgSO$_4$) and evaporated to give a white solid (0.51 g) which was dissolved in acetone (10 ml) and treated with sodium ethylhexanoate in methyl isobutyl ketone (1.1 equivalents). The resulting solid was filtered, washed with acetone (3 ml) and dried (0.4 g, 75%), $\nu_{max}$ (Nujol) 3300 (br), 1775, 1710, 1675 and 1605 cm$^{-1}$, δ (DMSO-d$^6$) 9.82 (1H, d, J 8 Hz, exch. D$_2$O), 9.14 (1H, d, J 9 Hz, exch D$_2$O) 7.60–7.20 (5H, m), 5.68 (1H, d, J 8 Hz, collapses to s on addition of D$_2$O), 5.43 (1H, dd, J 9 Hz and J 4 Hz, simplifies to d, J 4 Hz on addition of D$_2$O), 5.10 (1H, d, J 4 Hz), 4.70–4.41 (1H, m), 4.12–3.73 (2H, m) 3.70–3.21 (6H, m) and 1.07 (3H, t, J 8 Hz) ppm.

EXAMPLE 2

6β[D,2(4-Ethyl-2,3-dioxopiperazine-1-carbonylamino)-2(4-hydroxyphenyl)]acetamidobisnorpenicillanic acid (a) Benzyl 6β[D,2(4-ethyl-2,3-dioxopiperazine-1-carbonylamino)-2-(4-benzyloxycarbonyloxyphenyl)-]acetamidobisnorpenicillanate The title compound was prepared in an analogous manner to that described in Example 1(b) from a reaction between benzyl 6,β-aminobisnorpenicillanate* (0.56 g, 2 mmol) and D,2(4-ethyl-2,3-dioxopiperazine-1-carbonylamino)-2(4-benzyloxycarbonyloxyphenyl)acetyl chloride (1.0 g, 2 mmol) in the presence of dry pyridine (1.3 equivalents). After purification by column chromatography the yield obtained was (0.1 g, 14%), $\nu_{max}$ (CH$_2$Cl$_2$) 1800, 1720 and 1700 cm$^{-1}$, δ (acetone-d$^6$) 10.00 (1H, d, J 6 Hz), 7.62–6.94 (15H, m), 5.72–5.40 (2H, m), 5.30–5.11 (5H, m), 5.00–4.83 (1H, m), 4.12–3.22 (8H, m) and 1.19 (3H, t, J 7 Hz) ppm.

*Obtained from benzyl 6,β-phenoxyacetamidobisnorpenicillanate by the method described in Example 1(a). Benzyl 6,β-phenylacetamidobisnorpenicillanate is the preferred source of benzyl 6,β-aminobisnorpenicillanate, both regarding the yield and purity of this compound.

(b) 6β-[D,2(4-Ethyl-2,3-dioxopiperazine-1-carbonylamino)-2(4-hydroxyphenyl)]acetamidobisnorpenicillanic acid, sodium salt Benzyl 6,β[D,2(4-ethyl-2,3-dioxopiperazine-1-carbonylamino)-2(4-benzyloxycarbonyloxyphenyl)-]acetamidobisnorpenicillanate (0.17 g, 0.23 mmol) in tetrahydrofuran (3 ml), ethanol (1 ml) and water (1 ml) was shaken under an atmosphere of hydrogen with 10% palladium on charcoal (0.1 g) for 4 hours. The mixture was treated with more catalyst (0.1 g) and hydrogenated for an additional 4 hours when a further quantity of catalyst (0.1 g) was added and hydrogenation continued for 16 hours. Work-up as in Example 1(c) gave the title compound as a white solid (0.036 g, 30%), $\nu_{max}$ (Nujol) 3300, 1780, 1730, 1690 and 1600 cm$^{-1}$. δ (acetone-d$^6$) 10.01 (1H, d, J 7 Hz), 8.05 (1H, d, J 9 Hz), 7.42 (2H, d, J 8 Hz), 6.83 (2H, d, J 8 Hz), 5.84–5.34 (3H, m), 5.11 (1H, m), 4.20–3.21 (8H, m), and 1.20 (3H, t, J 7 Hz) ppm.

EXAMPLE 3

6,β[2(4-Ethyl-2,3-dioxopiperazine-1-carbonylamino)]-thien-2-ylacetamidobisnorpenicillanic acid

(a) Benzyl 6,β[2(4-ethyl-2,3-dioxopiperazine-1-carbonylamino)]-thien-2-ylacetamidobisnorpenicillanate The title compound was prepared, using a method analogous to that described in Example 1(b) above, from a reaction between benzyl 6,β-aminobisnorpenicillanate* (0.28 g, 1 mmol) and 2(4-ethyl-2,3-dioxopiperazine-1-carbonylamino)thien-2-ylacetyl chloride (0.51 g, 1.5 mmol) in the presence of dry pyridine (1.3 equivalents). The crude product was purified by column chromatography to give the desired ester (0.1 g, 26%) $\nu_{max}$ (CH$_2$Cl$_2$) 1800, 1720 and 1700 cm$^{-1}$, δ (acetone-d$^6$) 10.00 (1H, d, J 6 Hz), 7.64–6.95 (9H, m), 6.05–4.95 (6H, m), 4.22–3.34 (8H, m), and 1.25 (3H, t, J 7 Hz) ppm.

*As in Example 2(a).

(b) 6,β[2(4-Ethyl-2,3-dioxopiperazine-1-carbonylamino)]thien-2-ylacetamidobisnorpenicillanic acid, sodium salt Benzyl 6,β[2(4-ethyl-2,3-dioxopiperazine-1-carbonylamino)]thien-2-ylacetamidobisnorpenicillanate (0.18 g, 0.3 mmol) in tetrahydrofuran (3 ml), ethanol (1 ml) and water (1 ml) was shaken with 10% palladium on charcoal (0.2 g) under an atmosphere of hydrogen for 4 hours. A further quantity of catalyst (0.2 g) was then added and the mixture hydrogenated for an additional 4 hours. Work-up as in Example 1(c) gave the sodium salt as a white solid (0.04 g, 25%), δ (CD$_3$OD) 7.35–6.90 (3H, m), 5.91–5.24 (3H, m), 4.92 (1H, m), 4.12–3.41 (8H, m) and 1.22 (3H, t, J 7 Hz) ppm.

EXAMPLE 4

Sodium 6,β[D,2-4-Ethyl-2,3-dioxopiperazine-1-carbonylamino]-1-phenyl-acetamidobisnorpenicillanate

(a) Benzyl 6β[D,2(4-ethyl-2,3-dioxopiperazine-1-carbonylamino)]phenylacetamidobisnorpenicillanate To a stirred, cooled (CCl$_4$-solid CO$_2$) solution of benzyl 6β-phenoxyacetamidobisnorpenicillanate (0.824 g, 2 mmol) in dry dichloromethane (20 cm$^3$) was added N-methylmorpholine (0.44 cm$^3$) followed by the addition over 5 minutes of a solution of phosphorous pentachloride (0.5 g) in dry dichloromethane (15 cm$^3$). After stirring for a further 30 minutes, during which time the temperature was allowed to approach 0° C., the mixture was recooled (CCl$_4$-solid CO$_2$), treated with N-methylmorpholine (0.44 cm$^3$), followed by the dropwise addition of dry methanol (10 cm$^3$) over 5 minutes. After stirring at 0° to −5° C. for 2½ hours, the mixture was poured into ice water (60 cm$^3$) and the pH of the vigorously-stirred mixture adjusted to 2 using dilute ammonium hydroxide solution. After stirring vigorously at pH 2 for 20 minutes with cooling in an ice bath, the pH was adjusted to 6 using dilute ammonium hydroxide solution and the organic layer separated. The aqueous layer was re-extracted with dichloromethane (20 cm$^3$) and the combined organic fractions washed with saturated sodium bicarbonate solution (10 cm$^3$), followed by brine (3×20 cm$^3$). The separated organic layer was dried (MgSO$_4$), and concentrated to ca. 20 cm$^3$.

Freshly prepared D-2(4-ethyl-2,3-dioxopiperazine-1-carbonyl)amino phenylacetyl chloride, generated by the treatment of the corresponding acid (0.670 g, 2 mmol) with oxalyl chloride (0.254 g, 2 mmol) and N,N-dimethylformamide (1 drop) at 0° C. in dichloromethane (10 cm$^3$), was added to above solution at 0° C. with stirring, followed by pyridine (0.158 g, 2 mmol). After 90 minutes at 0° C., the reaction mixture was washed sequentially with dilute hydrochloric acid, dilute aqueous sodium hydrogen carbonate, and saturated brine. The dried (MgSO$_4$) organic layer was evaporated to give a yellow syrup which was purified using silica gel column chromatography to afford the product as a colourless gum (0.257 g, 22%).

(b) Sodium 6β[D,2(4-ethyl-2,3-dioxopiperazine-1-carbonylamino)]phenylacetamidobisnorpenicillanate To benzyl 6β[D,2-(4-ethyl-2,3-dioxopiperazine-1-carbonylamino)]phenylacetamidobisnorpenicillanate (0.209 g, 0.364 mmol) in THF (20 cm$^3$) was added distilled water until the solution turned cloudy. This solution was hydrogenated over 10% palladium/charcoal (0.200 g) for 2 hours at room temperature. The mixture was filtered through Kieselguhr and the THF evaporated. The aqueous solution was freeze-dried to give the title compound as an off-white amorphous solid (0.124 g, 70%). This material was further purified by covering a water (5 cm$^3$) suspension of the above solid with ethyl acetate. The pH of the solution was adjusted to 1.5 with vigorous stirring. The organic fraction was separated, dried (MgSO$_4$) and evaporated to give a white solid (0.038 g) which was taken up in the minimum quantity of ethyl acetate. A solution of 2 M—sodium ethyl hexanoate (0.04 cm$^3$) in methyl isobutyl ketone was then added, followed by dry ether (1 cm$^3$). The precipitated solid was filtered, washed well with dry ether, and dessicated to furnish the product (0.034 g, 19%) as an amorphous white solid.

BIOLOGICAL DATA

MIC values (μg/ml) of the compounds of Example 4b against a number of organisms important in human infections

| ORGANISM | Compound of Example 4b | |
|---|---|---|
| | AGAR | BROTH |
| E. coli JT4 | >100 | |
| E. coli JT425 | 10 | |
| E. coli NCTC 10418 | 1.0 | 0.5 |
| Ps aeruginosa 10662 | 10 | 10 |
| Ps aeruginosa 10662 10$^{-2}$ | 5.0 | 5.0 |
| Ps aeruginosa Dalgleish 10$^{-2}$ | >100 | |
| Serratia marcescens US32 | 0.5 | |
| Klebsiella aerogenes A | 0.2 | >10 |
| Enterobacter cloacae N1 | 0.5 | |
| P. mirabilis C977 | 0.1 | |
| P. mirabilis 889 | >100 | |
| P. morganii | 0.2 | |
| P. rettgeri | 0.5 | |
| B. subtilis | 5.0 | |
| Staph. aureus Oxford | 1.0 | 0.5 |
| Staph. aureus Russell | >100 | |
| S. faecalis I | 50 | |
| β-Haemolytic Strep. CN10 | 0.2 | |

I claim:

1. A compound of formula (I) or a pharmaceutically acceptable salt or in vivo hydrolysable ester thereof:

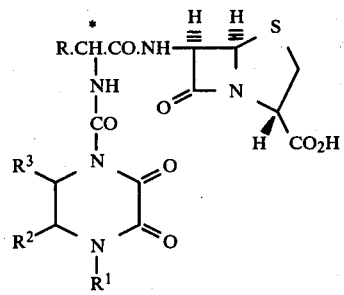

wherein R is phenyl, 4-hydroxy phenyl, or a 5- or 6-membered heterocyclic ring containing up to three heteroatoms selected from oxygen, sulphur or nitrogen, optionally substituted with hydroxy, amino, halogen or $C_{1-6}$ alkoxy;

$R^1$ represents hydrogen or $C_{1-6}$ alkyl;

$R^2$ and $R^3$ are the same or different and represent hydrogen, $C_{1-6}$ alkyl, halogen, amino, hydroxy, or $C_{1-6}$ alkoxy.

2. A compound as claimed in claim 1 wherein the carbon atom marked * in formula (I) is in the D configuration.

3. A compound as claimed in claim 1 wherein R is phenyl, 4-hydroxyphenyl, 2-thienyl, 3-thienyl or 2-amino-4-thiazolyl.

4. A compound as claimed in claim 1 wherein $R^1$, $R^2$ and $R^3$ may be the same or different and each represents methyl, ethyl, n- or isopropyl, n-, sec-, iso or tert-butyl.

5. A compound as claimed in claim 1 wherein $R^2$ and $R^3$ are hydrogen.

6. A compound as claimed in claim 1 wherein $R^1$ is ethyl.

7. A compound as claimed in claim 1 which is:
6,β[D,2(4-ethyl-2,3-dioxopiperazine-1-carbonylamino)]phenylacetamidobisnorpenicillanic acid;
6,β[2,4(ethyl-2,3-dioxopiperazine-1-carbonylamino)]-thien-2-ylacetamidobisnorpenicillanic acid; or
6,β[D,2(4-ethyl-2,3-dioxopiperazine-1-carbonylamino)-2-(4-hydroxyphenyl)]acetamidobisnorpenicillanic acid.

8. A pharmaceutical composition having antibacterial activity comprising an antibacterially effective amount of a compound as claimed in claim 1 together with a pharmaceutical carrier or excipient.

9. A pharmaceutical composition having antibacterial activity according to claim 8 which also comprises a compound of formula (VIII) or a pharmaceutically acceptable salt or ester thereof:

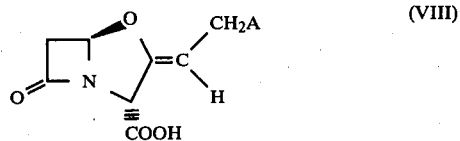

wherein A is hydroxyl, substituted hydroxyl, thiol, substituted thiol, amino, mono- or di-hydrocarbyl-substituted amino, or mono- or di-acylamino.

* * * * *